US006632682B1

(12) United States Patent
Ziegelmaier

(10) Patent No.: US 6,632,682 B1
(45) Date of Patent: Oct. 14, 2003

(54) ONE-STEP IMMUNOASSAY FOR THE DETERMINATION OF ANTIGEN-SPECIFIC ANTIBODIES OF ONE OF THE IMMUNOGLOBULIN CLASSES A, M, D, OR E, AND AN AGENT SUITABLE FOR THIS PURPOSE

(75) Inventor: Robert Ziegelmaier, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/445,584

(22) Filed: May 22, 1995

Related U.S. Application Data

(63) Continuation of application No. 07/988,007, filed on Dec. 9, 1992, now abandoned, which is a continuation of application No. 07/670,523, filed on Mar. 18, 1991, now abandoned, which is a continuation of application No. 07/434,472, filed on Nov. 14, 1989, now abandoned, which is a continuation of application No. 07/196,526, filed on May 20, 1988, now abandoned.

(30) Foreign Application Priority Data

May 23, 1987 (DE) .......................................... 37 17 401

(51) Int. Cl.[7] ............................................ G01N 33/543
(52) U.S. Cl. ..................... 436/513; 436/512; 436/518; 436/523; 436/538; 436/548; 436/820; 435/7.72; 435/7.9; 435/7.94; 435/962
(58) Field of Search ................................ 436/518, 523, 436/538, 548, 513, 512, 820; 435/7.72, 7.9, 7.94, 962

(56) References Cited

U.S. PATENT DOCUMENTS

| 4,130,634 A | * | 12/1978 | Molinaro et al. ............... 424/8 |
| 4,273,756 A | * | 6/1981 | Ling ........................ 436/513 X |
| 4,292,403 A | * | 9/1981 | Duermeyer .................... 435/5 |
| 4,347,311 A | * | 8/1982 | Schmitz ...................... 435/7 X |
| 4,434,227 A | * | 2/1984 | Unger ........................... 435/7 |
| 4,477,576 A | * | 10/1984 | Deutsch et al. ......... 436/548 X |
| 4,486,530 A | * | 12/1984 | David et al. ............ 436/548 X |
| 4,663,277 A | | 5/1987 | Wang |
| 4,962,023 A | * | 10/1990 | Todd et al. .................... 435/7 |

FOREIGN PATENT DOCUMENTS

| EP | 0-008-473 A1 | 3/1980 |
| EP | 0-083-869 A1 | 7/1983 |
| EP | 0061167 | 7/1985 |
| EP | 0-163-312 A2 | 12/1985 |
| EP | 0-261-493 A2 | 3/1988 |
| GB | 2-026-691 A | 2/1980 |

OTHER PUBLICATIONS

H. Schmitz, Detection of IgM Antibodies to Cytomegalovirus Using an Enzyme—Labelled Antigen, 1980, V. 50, p 59–68.*
Duermeyer W. Enzyme Linked Immunosorbent Assay for Detection of Immunoglobulin M Antibodies Against *Toxoplasma gondii* 1980, 12/6, 805–806.*
Wiellaard, F, Diagnosis of Acute Toxoplasmosis by an Enzyme Immunoassay for Specific Immunoglobulin M Antibodies 1983, 17/6, 981–987.*
Sachers, M. et al., J. Virological Methods, 10:99–110 (1985).
Schmitz, H. et al., J. Gen. Virol., 50:59–68, 1980.
Nakane, P.K. et al., "Peroxidase–Labeled Antibody A New Method of Conjugation" J. Histochem. Cytochem.: 22(12); 1084–1091 (1974).
Ishikawa, E. et al., "Enzyme–Labeling of Antibodies and Their Fragments for Enzyme Immunoassay and Immunohistochemical Staining", J. Immunoassay, 4(3): 209–327 (1983).
Bergmeyer, Methods of Enzymatic Analysis, Vol. X, Antigens and Antibodies 1, pp. 292–308 (3rd ed. 1986).

* cited by examiner

Primary Examiner—Bao Thuy L. Nguyen
(74) Attorney, Agent, or Firm—Finnegan, Henderson, Farabow, Garrett and Dunner, L.L.P.

(57) ABSTRACT

An immunochemical method for the determination of antibodies which are specific for an antigen and are of one of the immunoglobulin classes: A, M, D or E in a fluid, with this fluid being contacted with a solid phase to which the antibodies against this immunoglobulin class, or a fragment of an antibody of this type, are bound, which results in the immunoglobulin of this class being bound to this solid phase, and this solid phase being contacted with the antigen, which carries a labeling means where appropriate, and with a labeled antibody or a labeled fragment of an antibody against the antigen if the antigen is unlabeled and determination, from the amount of labeling means which is bound to the solid phase, of the amount of these antibodies which are specific for an antigen and are one of the immunoglobulin classes, which comprises the solid phase being simultaneously in contact with the fluid containing the antibody which is to be determined and with the antigen, which is labeled where appropriate, there being addition of a substance which prevents immunoglobulin G binding to the solid phase and, where appropriate, antigen binding to immunoglobulin G, and an agent suitable for this purpose, are described.

16 Claims, No Drawings

ONE-STEP IMMUNOASSAY FOR THE DETERMINATION OF ANTIGEN-SPECIFIC ANTIBODIES OF ONE OF THE IMMUNOGLOBULIN CLASSES A, M, D, OR E, AND AN AGENT SUITABLE FOR THIS PURPOSE

This application is a continuation application filed May 22, 1995 of parent application U.S. Ser. No. 07/988,007, filed Dec. 9, 1992, now abandoned, which is a continuation application of Ser. No. 07/670,523 filed Mar. 18, 1991, now abandoned, which is a continuation application of Ser. No. 07/434,472 filed Nov. 14, 1989, now abandoned, which is a continuation application of Ser. No. 07/196,526 filed May 20, 1988, now abandoned.

The invention relates to an immunochemical method for the detection and for the determination of antibodies which are specific for a particular antigen and are of one of the immunoglobulin classes. This method is suitable for the highly sensitive and specific detection and for the determination of antibodies of one of the immunoglobulin classes A, M, D or E.

Immunoglobulins are antibodies formed by the immune system of the body against foreign substances (antigens, for example proteins of pathogens, bacterial polysaccharides, serum proteins, tissue proteins or other immunoglobulins). The immunoglobulin molecule is composed of one or more sets of 4 polypeptide chains, two heavy chains each having a molecular weight of about 53,000 daltons and two light chains each of about 22,000 daltons, which are connected by disulfide bridges.

Immunoglobulins are generally assigned to the classes G, A, M, D or E and, correspondingly, called IgG, IgA, IgM, IgD or IgE. These 5 immunoglobulin classes differ in the antigenic determinants of the heavy chain, which are called gamma-, alpha-, mu-, delta- and epsilon-chains; in addition, there are also immunoglobulin subclasses of IgG, IgA and IgM.

Immunoglobulins can be split into fragments which retain the antigen-binding property or into fragments without the antigen-binding property. Examples of antigen-binding fragments are Fab, Fab' and F(ab')$_2$ fragments. Examples of fragments without the antigen-binding property are Fc and Fc' fragments.

The concentrations of immunoglobulins in normal human serum are (in mg/ml): IgG 8–16, IgA 1.4–4, IgM 0.5–2, IgD 0.0–0.4 and IgE 0.000017–0.00045.

The immunoglobulins present in the highest quantity in human serum are those of the IgG class. Immunoglobulins of the IgM class appear very soon after an infection, for which reason their determination is important for the early diagnosis of an infectious disease or for the diagnosis of an acute infection.

The second most abundant immunoglobulins are of the immunoglobulin class IgA and are the most important secretory antibodies.

Immunoglobulins of classes IgD and IgE can be found in elevated concentration in certain pathological processes; for example IgE has properties which sensitize mast cells and it plays a significant part in the pathogenesis of a number of allergic reactions. IgD antibodies are found in autoimmune diseases.

The determination of antigen-specific immunoglobulins, especially of a particular class, is of special importance for detecting particular diseases caused by parasites, bacteria or viruses, it being possible in this connection to distinguish between acute and resolved infections and, where applicable, to draw conclusions about the prognosis.

A large number of immunological methods is known for the determination of immunoglobulins. Methods for the physical separation of immunoglobulins into classes, for example immunodiffusion, immunoelectrophoresis or density gradient centrifugation, are elaborate, inaccurate and susceptible to interference.

Antigen-specific immunoglobulins can be determined in what is called the direct method by immunoassay techniques; these entail an immune component with binding affinity for the antibody class which is to be determined being coupled to a solid carrier, for example antibodies against the $\mu$-chain of human IgM, and the antigen-specific immunoglobulin fraction being detected either by labeled antigen or as a combination of unlabeled antigen and antigen-specific labeled antibody. The fraction of the labeled immune component which is bound to the solid phase and is directly proportional to the concentration of the antibody which is to be detected is measured.

Used for the labeling are, for example, fluorescent and chromophoric substances or radioactive isotopes, enzymes or particles loaded with immune components, such as erythrocytes or latex particles; it is also possible to use a biological function of the antigen used, for example hemolysis, to indicate that reaction has taken place.

A disadvantage of the methods of the state of the art is that the non-antigen-specific immunoglobulin fraction of any particular immunoglobulin class enters into competition with the antigen-specific fraction for the relevant antibody on the solid phase. This may mean that results differ depending on the ratio of these amounts, even if the antigen-specific antibody fraction remains unchanged (the non-antigen-specific immunoglobulin fraction may in such cases vary by a factor of 5 or more).

It is essential in all the so-called direct and indirect methods which have been described and quoted hitherto that, after reaction (incubation) of the sample with the immune component on the solid carrier and before reaction with the detecting immune component, unbound material is removed by washing. This is why these methods are called "two-step methods".

Hence, an assay with a ready-to-use carrier-bound component requires at least three reaction steps (sample/second immune component/detection reaction) which are separated from one another by at least 2 washing steps, each reaction step itself requiring a certain reaction time so that the sum thereof gives the total assay time.

The object now was to shorten and simplify the direct assay and to eliminate the competition between non-antigen-specific and antigen-specific immunoglobulins in order to permit reliable quantitative determination of the antigen-specific antibody fraction.

It has now been found, surprisingly, that this is possible by contacting carrier-bound immune component, analyte-containing sample and labeled detecting immune component without washing between addition of the sample and addition of the labeled detecting immune component.

This "one-step method" has become possible after successful elimination of two possible interferences:

In the first place, the effect of antigen-specific IgG antibodies must be eliminated so that the reaction thereof with the antigen, which would interfere with the actual detection method, is now zero or only inconsiderable. This interference is possible in principle because, in the determination of antigen-specific antibodies of one of the immunoglobulin classes IgA, IgM, IgE or IgD, there are as a rule also present, and in general in a higher concentration, antigen-specific IgG antibodies in the patient's sample.

In the second place, the activity of rheumatoid factors (RF), that is to say antibodies against IgG which belong to various immunoglobulin classes, has to be suppressed because it can lead to falsification of the result. This falsification is possible because RF are bound to the antibody on the solid phase, and bound over the antigen-specific IgG antigen which is bound by the RF in turn, and thus a false-positive detection reaction is obtained.

It has been possible to eliminate both possibilities of interference by, for example, addition of anti-human IgG, gamma-chain ("RF adsorbent" of Behringwerke AG) to the sample (for example serum).

The invention relates to an immunochemical method for the determination of antibodies which are specific for an antigen and are of one of the immunoglobulin classes A, M, D or E in a fluid, with this fluid being contacted with a solid phase to which the antibodies against this immunoglobulin class, or a fragment of an antibody of this type, are bound, which results in the immunoglobulin of this class being bound to this solid phase, and this solid phase being contacted with the antigen, which carries a labeling means where appropriate, and with a labeled antibody or a labeled fragment of an antibody against the antigen if the antigen is unlabeled, and determination, from the amount of labeling means which is bound to the solid phase, of the amount of these antibodies which are specific for an antigen and are of one of the immunoglobulin classes, which comprises the solid phase being simultaneously in contact with the fluid containing the antibody which is to be determined and with the antigen, which is labeled where appropriate, there being addition of a substance which prevents immunoglobulin G binding to the solid phase and, where appropriate, antigen binding to IgG.

Examples of a substance of this type are an antibody against the gamma-chain of human immunoglobulin G (anti-human IgG, gamma-chain), aggregated human or animal IgG or a gamma Fc fragment, preferably anti-human IgG, gamma-chain. These substances can also be used in combination to enhance the effect.

A substance of this type, preferably anti-human IgG, gamma-chain (RF adsorbent of Behringwerke Ag) can be added, for example, to the sample dilution buffer, preferably in an amount which complexes on average 15 mg/ml of IgG in the serum (based on undiluted sample).

This measure makes a one-step method possible, and the sample can be assayed in a dilution (for example 1:700) which is a factor of 3 to 8 higher than in the two-step method of the state of the art (assay dilution 1:100 to 1:200).

At the same time, the competition which has been mentioned is virtually eliminated, which makes correct and reproducible measurement possible, and allows a higher detection sensitivity to be achieved (see Table 2).

A preferred embodiment of the method according to the invention is one in which labeled antigen is used.

However, it is also possible to use unlabeled antigen and a labeled antibody which is directed against this antigen, or a labeled fragment of an antibody of this type.

Used for the labeling are, for example, fluorescent and chromophoric substances or radioactive isotopes, enzymes or particles loaded with immune components, such as erythrocytes or latex particles; it is also possible to use a biological function of the antigen used, for example hemolysis, to indicate that reaction has taken place.

An enzyme is preferably used.

Antibodies against immunoglobulin class M, or fragments of such antibodies which have retained the reactivity with these immunoglobulins, are preferably bound to the solid phase.

The method according to the invention is preferably used for the determination of antibodies directed against hepatitis B core protein, against antigens of hepatitis A virus, human immunodeficiency virus (HIV), rubella virus or cytomegalovirus, or antigens of *Treponema pallidum* or *Toxoplasma gondii*.

The invention also relates to an agent for carrying out the method according to the invention, which is composed at the least of a carrier to which antibodies specific for one of the human immunoglobulin classes are bound, of labeled antigen for which this immunoglobulin is specific, and reagents for the detection or for the determination of the labeling.

An agent of this type is preferably composed at the least of a carrier to which antibodies specific for human IgM are bound, antigen, labeled antigen-specific antibodies and reagents for the detection of the labeling.

Also preferred is an agent of this type which is composed of a single element which contains, in the dry form, all the reagents which are required for the method.

Suitable carrier materials for the solid phase are synthetics such as polystyrene, polyvinyl chloride, polyamide or other synthetic polymers, natural polymers such as cellulose, as well as derivatized natural polymers such as cellulose acetate or nitrocellulose, and glass, especially glass fibers.

The carriers can take the form of spheres, rods, tubes and microassay plates. Sheet-like structures such as paper strips, small plates and membranes are likewise suitable. The surface of the carriers can be both permeable and impermeable for aqueous solutions.

Preferred carriers are microassay plates.

A solid phase suitable for the method according to the invention is produced by irreversibly binding an antibody preparation to a carrier. The term "solid phase" in the present text is employed both for the carrier itself and for the carrier with the immunochemical reactant bound thereto.

Irreversible binding within the meaning of the invention is present when, for example, there is
1) adsorptive binding which is not cleaved by the agents used in the method, such as labeled immunological reagents, dilution solutions or buffer solutions,
2) bioaffinity binding which is mediated by an immunochemically (high-affinity antibodies) or non-immunochemically binding spacer, it being possible for the spacer to be composed of biotin and avidin or other conjugates of receptors and ligands,
3) a direct covalent bond, or
4) a covalent bond which is mediated by a bifunctional chemical spacer.

The covalent bond is preferred in the case where water-permeable carriers are used, and the adsorptive binding is preferred in the case where water-permeable as well as water-impermeable carriers are used.

Direct adsorptive binding of antibody preparations to a carrier which takes the form of polystyrene treated with gamma rays is particularly preferred.

For the antibody labeling it is possible to use monoclonal or polyclonal antibodies, as well as antigen-binding fragments thereof, which are obtained by methods described as state of the art.

Suitable antigens for the preparation of labeled antigens are classically purified proteins, synthetic peptides, or proteins prepared by genetic manipulation, whose preparation is described as state of the art.

The labeling is carried out by methods described as state of the art for the said labels.

In the case of labeling of the antibodies with peroxidase as enzyme, it is possible to use the periodate technique (J.

Histochem. Cytochem. 1974, 22, 1084–1090) or a method reported in J. Immunoassay (1983) 4, 209–327, in which the partners are linked with a heterobifunctional reagent.

The possible uses of the described invention of a one-step immunoassay are, in principle, identical to the uses of the direct and indirect multi-stage assays which have already been described previously. The present new method differs advantageously from the latter in three ways: The simultaneous incubation of analyte-containing sample and labeled immunological reagents dispenses with one incubation step and one washing procedure, which results in a considerable simplification of the assay procedure.

As is evident from the quoted example, the one-step method permits a considerable shortening of the overall duration of the assay, which has a great importance, besides the prime advantage of the practicability of the procedure for the method, for the rapid detection of acute infections in hospitals.

In the third place, this one-step method makes it possible to examine the sample at a high assay dilution, which results in elimination of possible competition and thus permits reliable, reproducible determination with, at the same time, higher detection sensitivity for antigen-specific immunoglobulins.

The example which follows presents one embodiment of the invention without intending to restrict it thereto.

EXAMPLE

Determination of Toxoplasma-specific immunoglobulin M in human serum

A. Preparation of polyclonal anti-human IgM Goat anti-human IgM was prepared as described in Methods of Enzymatic Analysis, 3rd edition 1986, Volume X, Antigens and Antibodies 1, Editor in Chief: Hans Ulrich Bergmeyer, p. 292–308.

B. Preparation of Toxoplasma antigen

*Toxoplasma gondii* parasites were grown in the abdominal cavity of mice for 3 days. After the mice had been sacrificed the parasites were obtained by irrigation of the abdominal cavity with phosphate-buffered saline, pH 7.2, washed by repeated sedimentation by centrifugation, and resuspended. A suspension prepared in this way was sonicated with cooling, and centrifuged, and the supernatant was used as antigen for the enzyme-labeling.

C. Enzyme-labeling of the antigen
   a) 20 mg of peroxidase (POD) were taken up in 0.5 ml of phosphate-buffered saline (PBS), pH 7.0, and activated by addition of 0.6 ml of sodium periodate. After about 30 min at room temperature, the excess periodate was removed by chromatography (Sephadex G25), and the brown-green eluate (activated POD) was collected.
   b) Coupling of the peroxidase to the antigen 1 part by weight of Toxoplasma antigen with saline/carbonate buffer, pH 9.5, was mixed with two parts by weight of activated peroxidase. Incubation at room temperature for 2 h was followed by the Schiff bases which had formed being reduced by addition of sodium borohydride (1 mg/1 mg POD). The colored conjugate was stabilized by addition of 1 mg/ml phenol and 2% bovine serum albumin. The optimal dilution for use in the assay was determined by checkerboard titration, entailing evaluation of Toxoplasma IgM-positive and -negative sera with various concentrations of the antigen/peroxidase conjugate in the one-step assay as described in section E. The optimal concentration was chosen to be that at which the difference between the signals for the positive and negative samples was largest.

D. Coating of polystyrene microtiter plates with anti-human IgM

Irradiated polystyrene microtiter plates (as described in European Patent 0,061,167) were incubated with 100 µl of a solution of anti-human IgM in phosphate-buffered saline, pH 7.5, in each well at room temperature for several hours. The optimal concentration of the antibody solution was determined beforehand by serial dilution and testing of this sample coating. The plates were then sucked empty, washed with phosphate-buffered saline, dried with silica gel and packaged air- and moisture-tight.

E. Determination of Toxoplasma IgM antibodies using the one-step method according to the invention
   a) One serum sample, and one Toxoplasma IgM-positive and one Toxoplasma IgM-negative control sample were each diluted 1:350 with 0.3 mol/l Tris buffer solution, pH 7.5, containing 5 ml/100 ml bovine serum free of Toxoplasma antibodies, 0.1 ml/100 ml $^R$Tween 20 (polyoxyethylene sorbitan monolaurate) and antibodies against human IgG (gamma-chain) in a concentration such that 50 mg/ml IgG, based on the undiluted sample, are bound;
   b) 50 µl of each of these were placed in separate wells of the coated microtiter plates into which 50 µl of peroxidase-labeled Toxoplasma antigen had previously been placed in each well, in the optimal concentration determined beforehand by checkerboard titration, in the same buffer;
   c) the assay plate was covered and incubated at 37° C. for 2 h;
   d) the contents were then removed by aspiration, and 3 washes with PBS containing 0.1 ml/100 ml $^R$Tween 20 were carried out;
   e) now 100 µl of chromogen (o-phenylenediamine-HCl) in citrate/phosphate buffer, pH 5.5, were placed in each well, and incubation was carried out at room temperature for 30 min;
   f) thereafter, 100 µl of 1 normal sulfuric acid were placed in each well to stop the enzymatic conversion of substrate, and the solutions were measured in a photometer at 492 nm.
   g) Examples of results obtained:

TABLE 1

|  | Milliextinction (mE 492 nm) |
| --- | --- |
| strongly positive control | 1080 |
| weakly positive control | 314 |
| negative control | 58 |
| positive sample | 1302 |
| negative sample | 104 |

A sample is to be regarded as positive if its value is above the extinction of the negative control plus 100 mE (158 mE in the example).

F. Determination of IgM antibodies using the two-step method of the state of the art The same peroxidase-labeled Toxoplasma antigen, whose preparation is described in section Cb) of the example, and the same microassay plates, whose preparation is described in section D of the example, were used.
   a) The serum samples listed in Table 2 were each diluted 1:200 with 0.3 mol/l Tris buffer solution, pH 7.5, containing 5 ml/100 ml bovine serum free of Toxoplasma antibodies, and 0.1 ml/100 ml $^R$Tween 20 (polyoxyethylene sorbitan monolaurate);

b) 50 μl of each of these were placed in separate wells of the coated microassay plate;

c) the assay plate was covered and incubated at 37° C. for 1 h;

d) the contents were removed by aspiration, and 3 washes with PBS containing 0.1 ml/100 ml $^R$Tween 20 were carried out;

e) then 50 μl of peroxidase-labeled Toxoplasma antigen were placed in each well;

f) the assay plate was covered again and incubated at 37° C. for 2 h;

g) thereafter the contents were removed by aspiration, and 3 washes with PBS containing 0.1 ml/100 ml $^R$Tween 20 were carried out;

h) 100 μl of chromogen (o-phenylenediamine-HCl) in citrate/phosphate buffer, pH 5.5, were placed in each well, and incubation was carried out at room temperature for 30 min;

i) thereafter, 100 μl of 1 normal sulfuric acid were placed in each well to stop the enzymatic conversion of substrate, and the solutions were measured in a photometer at 492 nm;

The serum samples listed in Table 2 were also treated by the one-step method described in sections Ea) to Ef).

The results of the two methods are shown in Table 2.

TABLE 2

| | Milliextinction (mE 492 nm) | |
| --- | --- | --- |
| | One-step method Assay duration 2.0 h | Two-step method Assay duration 3.5 h |
| Pos. control | 1,400 (1,600) | 2,300 |
| Neg. control | 88 (141) | 136 |
| Patients' sera | | |
| 1 | 204 (145) | 155 |
| 2 | 498 (127) | 133 |
| 3 | 495 (102) | 159 |
| 4 | 499 (110) | 123 |
| 5 | 466 (113) | 118 |
| 6 | 466 (158) | 202 |
| 7* | 1480 (428) | 621 |

( ) Extinctions obtained in the one-step method without addition of RF adsorbent
*Contains 30 g/l IgG It is evident from the measured values for the extinction, which are a measure of the content of Toxoplasma IgM antibodies in the sera, that the one-step method provides positive results for patients' sera 1–6 (mE$_{492\,nm}$ greater than 88 plus 100) which gave negative results in the two-step method (mE$_{492\,nm}$ less than 136 plus 100).

The omission of RF adsorbent in the one-step method gives rise to false-negative values for many sera, for example sera 1–6, or low values, for example for serum 7, as is evident from the figures in parentheses.

Accordingly, detection of Toxoplasma IgM antibodies using the one-step method is more sensitive, and the detection of the said antibodies, and others, can be carried out more rapidly and straightforwardly, as is shown by comparison of the effort involved in the two methods, which is evident from sections E and F.

What is claimed is:

1. An immunological method for the detection of an antigen specific antibody comprising one or more of the immunoglobulin classes A, M, D, or E in a fluid, comprising the simultaneous incubation of:

a. a solid phase having bonded thereto an antibody specific for said immunoglobulin classes A, M, D, or E;

b. a fluid containing an immunoglobulin of classes A, M, D, or E;

c. an unlabeled antigen immunologically reactive to the fluid phase immunoglobulin;

d. a labeled antibody, immunologically reactive with said unlabeled antigen; and e. a substance which inhibits the binding of immunoglobulin G to the solid phase and which inhibits the binding of said unlabeled antigen to immunoglobulin G.

2. The method as claimed in claim 1, wherein anti-human IgG, aggregated human IgG, or a gamma Fc fragment is added.

3. The method as claimed in claim 1, wherein one or both antibodies are monoclonal antibodies or fragments of monoclonal antibodies.

4. The method as claimed in claim 1, wherein the antibodies which are to be determined are those of immunoglobulin class M directed against hepatitis B core protein, antigens of hepatitis A virus, human immunodeficiency virus, rubella virus, cytomegalovirus, proteins of *Treponema pallidum*, or proteins of *Toxoplasma gondii*.

5. The method as claimed in claim 1, wherein the labeled antibody is labeled with an enzyme.

6. The method as claimed in claim 1, wherein the labeled antibody is labeled with erythrocytes.

7. The method according to claim 1, further comprising using reagents for the detection or determination of the label if the label itself is not directly detectable.

8. The method according to claim 1, further comprising using all reagents combined together in a single analytical element in dry form.

9. An immunological method for the detection of an antigen specific antibody comprising one or more of the immunoglobulin classes A, M, D or E in a fluid, comprising the simultaneous incubation of:

a. a solid phase having bonded thereto an antibody specific for said immunoglobulin classes A, M, D, or E;

b. a fluid containing an immunoglobulin of classes A, M, D, or E;

c. a labeled antigen immunologically reactive to the fluid phase immunoglobulin; and d. a substance which inhibits the binding of immunoglobulin G to the solid phase and which inhibits the binding of said labeled antigen to immunoglobulin G.

10. The method as claimed in claim 9, wherein the substance which prevents immunoglobulin G from binding to the solid phase comprises anti-human IgG, aggregated human IgG or a gamma-Fc fragment.

11. The method as claimed in claim 9, wherein once or both antibodies are monoclonal antibodies or fragments monoclonal antibodies.

12. The method as claimed in claims 9, wherein the antibodies which are to be determined are those of immunoglobulin class M and are directed against hepatitis B core protein, antigens of hepatitis A virus, human immunodeficiency virus, rubella virus, cytomegalovirus, proteins of *Treponema pallidum*, or proteins of *Toxoplasma gondii*.

13. The method as claimed in claim 9, wherein the labeled antigen is labeled with an enzyme.

14. The method as claimed in claim 9, wherein the labeled antigen is labeled with erythrocytes.

15. A method according to claim 9, further comprising reagents for the detection or determination of the label if the label itself is not directly detectable.

16. The method according to claim 9, further comprising all reagents combined together in a single analytical element in dry form.

* * * * *

UNITED STATES PATENT AND TRADEMARK OFFICE
CERTIFICATE OF CORRECTION

PATENT NO. : 6,632,682 B1 Page 1 of 1
DATED : October 14, 2003
INVENTOR(S) : Robert Ziegelmaier It is certified that error appears in the above-identified patent and that said Letters Patent is hereby corrected as shown below:

<u>Column 8,</u>
Line 48, "once" should read -- one --.
Lines 49-50, "fragments monoclonal" should read -- fragments of monoclonal --.
Line 51, "claims" should read -- claim --.

Signed and Sealed this

Fifteenth Day of June, 2004

JON W. DUDAS
*Acting Director of the United States Patent and Trademark Office*